United States Patent [19]

Bouniot et al.

[11] 4,377,685
[45] Mar. 22, 1983

[54] PROCESS OF PREPARING SUCROGLYCERIDES

[75] Inventors: Albert Bouniot; Robert Couraud, both of Melle; Guy Lartigau, Savigny-sur-Orge, all of France

[73] Assignee: Rhone-Poulenc Industries, Paris, France

[21] Appl. No.: 177,209

[22] Filed: Aug. 11, 1980

[30] Foreign Application Priority Data

Aug. 16, 1979 [FR] France .................. 79 20758

[51] Int. Cl.³ ............................... C07H 13/02
[52] U.S. Cl. ....................................... 536/119
[58] Field of Search ......................... 536/115–119, 536/1

[56] References Cited

U.S. PATENT DOCUMENTS

| | | | |
|---|---|---|---|
| 2,812,324 | 11/1957 | Huber et al. | 260/234 |
| 2,831,855 | 4/1958 | Martin | 260/234 |
| 2,831,856 | 4/1958 | Tucker | 260/234 |
| 3,480,616 | 11/1969 | Osipow et al. | 536/119 |
| 3,644,333 | 2/1972 | Osipow et al. | 260/234 R |
| 3,714,144 | 1/1973 | Feuge et al. | 260/234 R |
| 3,996,206 | 12/1976 | Parker et al. | 536/119 R |
| 4,010,183 | 3/1977 | Quesda | 260/428.5 |

FOREIGN PATENT DOCUMENTS 612041 8/1961 Belgium .
650389 12/1962 Italy .

OTHER PUBLICATIONS

L. Bobichon, "A Sugar Ester Process And Its Applications In Calf Feeding And Human Food Additives", in *Sucrochemistry*, (J. L. Hickson ed.), ACS Symposium Series 41, pp. 115–120, at 115–119 (1977).

L. Osipow and W. Rosenblatt, "Micro-Emulsion Process For The Preparation Of Sucrose Esters", *Jour. Amer. Oil Chemists Soc.*, 44, pp. 307–309 (1967).

T. Kosaka and T. Yamada, "New Plant And New Application Of Sucrose Esters", in *Sucrochemistry* (J. L. Hickson ed.), ACS Symposium Series 41, pp. 84–96, at 84–88 (1977).

K. J. Parker et al., "Sucrose Ester Surfactants-A Solventless Process And The Products Thereof", in *Sucrochemistry* (J. L. Hickson ed.), ACS Symposium Series 41, pp. 97–114, at 96–105 and 113 (1977).

*Primary Examiner*—Blondel Hazel

[57] ABSTRACT

A method of preparing sucroglycerides by transesterification of sucrose and a triglyceride, whereby there is conducted a limited alcoholysis of the triglyceride before reaction with the sucrose. The sucroglycerides obtained have interesting emulsifying properties and can be used to advantage in foodstuffs.

24 Claims, No Drawings

PROCESS OF PREPARING SUCROGLYCERIDES

BACKGROUND OF THE INVENTION

The present invention relates to a process of preparing sucroglycerides.

It is known that the expression "sucroglyceride" designates the mixture of products obtained by reaction of sucrose with natural or synthetic triglycerides, which mixture contains monoglycerides, diglycerides, unchanged triglycerides (in small amounts), monoesters and diesters of sucrose in variable proportions depending on the nature of the triglyceride used and the proportion thereof employed with respect to the sucrose. Thus it is possible for the sucrose to be combined in a form ranging from monoesters to octaesters.

The term "combined sucrose" is understood by those skilled in the art to mean sucrose in its esterified form. As used herein, the term "sucrose" is used synonymously with the term "saccharose" and is intended to include sugar whether from beet or cane sources.

The sucroglycerides have interesting emulsifying properties due, in particular, to the sucrose mono- and diesters and the monoglycerides. These nonionic emulsifiers are completely biodegradable, non-toxic, odorless, tasteless, and well tolerated by living organisms. Consequently, they are used in human and animal foodstuffs and in numerous other fields of use, such as for example, household or industrial detergents, cosmetics, etc.

The reaction of transesterification of the triglycerides and sucrose, leading to liberating alcohol functions of the glycerol, is an equilibrium reaction which is difficult to displace, as a result of the high boiling point of the glycerol and the fact that properties analogous to sucrose make separation difficult.

The result is that the product obtained depends on the chemical equilibrium present between the sucrose and the glycerol in the reaction phase, which equilibrium is related to the concentration of the substances in this phase. However, as sucrose and the triglycerides are practically insoluble in each other, the reaction appears theoretically impossible in the absence of a common solvent which permits a certain concentration of the reagents in the reaction phase or phases.

Common solvents are rare and the one most commonly used in dimethylformamide. Indeed, it has been proposed to carry out the transesterification of sucrose and natural triglycerides in dimethylformamide, in the presence of anhydrous potassium carbonate, the reaction temperature being about 95° C. (See Italian Pat. No. 650,389). However, some traces of dimethylformamide or its derivatives always remain in the resultant sucroglycerides and these traces may be disturbing from a physiological viewpoint.

The use of other solvents has been recommended, such as pyridine, (U.S. Pat. No. 2,831,855), derivatives of morpholine or piperidine (U.S. Pat. No. 2,831,856) and dimethylsulfoxide (U.S. Pat. No. 2,812,324), but these solvents are scarcely any more satisfactory for use in foods.

More recently, research has been done on solventless processes which use either a fine dispersion of sucrose (Patent of Addition to French Pat. No. 2,029,508-69/15314), or a high temperature such as 190° C. (French Pat. No. 2,047,603-70/17075), or very long reaction times of about 10 to 20 hours (French Patent No. 2,221,436-74/08639). These processes are characterized by the presence of large amounts of 20 to 25%, or even more, of emulsifying agents or their precursors (soaps or potassium carbonate which produces soaps). The product obtained at the end of the reaction is highly colored thus showing the decomposition of the sucrose and contains a large amount of soaps while having relatively little combined sucrose.

For use in foods, it is desirable not to have more than 6% soaps in the emulsifiers. Therefore, it is desirable to provide a method for the industrial production of sucroglycerides which contain a minimum amount of soaps, thus making possible an increase in weight yield since the presence of surplus amounts of soaps must be eliminated by costly purification methods.

A method of manufacturing sucroglycerides has now been found in accordance with the present invention, which, in its optimal form, leads to the obtaining of sucroglycerides suitable without further treatment for food use since non-toxic compounds are used and there is a formation of a minimal amount of soaps. Also, the operating conditions of the process are such they they lead to a low carmelization of the sucrose.

It is, accordingly, an object of the present invention to provide a novel and effective process for producing sucroglycerides which process eliminates many of the disadvantages of prior art processes.

It is a further object of the invention to provide a useful and effective process for producing sucroglycerides which can be used, without extended purification, in foods.

Other objects of the invention will be apparent to those skilled in the art from the present disclosure.

GENERAL DESCRIPTION OF THE INVENTION

The present of the present invention for preparing sucroglycerides employs transesterification of sucrose and a triglyceride in which there is a first employed a limited alcoholysis of the triglyceride before reacting it with the sucrose. By the term "limited alcoholysis", it is understood the refer to the release of one, two or three alcohol functions from the triglyceride.

The process of the invention takes place in two steps. These steps involve reacting:

(I)—a triglyceride and an alcohol in the presence of an alcoholysis catalyst at a temperature of between about 80° and 180° C., optionally under pressure, (II)—thereupon, the sucrose and a basic transesterification catalyst in the reaction medium, which already contains a potassium soap, and the treated triglyceride from step (I), at a temperature between about 120° and 145° C., optionally under reduced pressure.

By "triglyceride", there is understood to mean one or more triglycerides of saturated or unsaturated aliphatic fatty acids, having at least about 12 carbon atoms and, preferably, about 14 to 20 carbon atoms. A synthetic triglyceride obtained by reaction of glycerol and fatty acids can obviously be used in accordance with the invention, but it is more interesting for economic reasons to employ natural triglycerides, which generally exist as mixtures.

As triglycerides which are suitable for the invention mention may be made, by way of example, of lard, tallow, peanut oil, butter fat, cotton seed oil, linseed oil, coconut oil, olive oil, palm oil, grapeseed oil, fish oil, soya oil, castor oil, etc.

Fatty acid triglycerides containing not more than one double bond are preferably used and, if necessary, they are subjected to hydrogenation in order to reduce the number of unsaturations. Therefore, hydrogenated natural substances can be used, such as, for instance, hydrogenated tallow.

There are various imperatives which determine the selection of the triglyceride used. Aside from the cost of the raw material, which constitutes a criterional choice which is not neglible, the use to be made of the sucroglycerides obtained is a factor. In fact, if they are used in the field of foodstuffs it is obviously necessary to select a triglyceride which does not have any harmful physiological effect, since some traces thereof always remain in the mixture or product obtained. In the list of said triglycerides, many are suitable for food use but recourse will preferably be had to palm oil which contains triglycerides of palmitic, oleic and linoleic acids and to tallow which contains triglycerides of oleic, steric and palmitic acids.

As an alcohol capable of being used to effect the partial alcoholysis of the triglyceride, one may employ the primary aliphatic monohydroxyl alcohols having from about 1 to 8 carbon atoms, such as, for instance, methanol, ethanol, hexanol and octanol and/or the polyhydroxyl alcohols having from about 1 to 8 carbon atoms and about 2 to 6 hydroxyl groups, such as ethyleneglycol, glycerol, erythritol, pentaerythritol, manitol and sorbitol, etc.

It is of interest to use a volatile alcohol, such as methanol or ethanol, since they can be eliminated by distillation during the second step of the process. This makes it possible to avoid an additional purification step. When it is desired to prepare sucroglycerides for food use, it is preferable to use ethanol, due to its low toxicity. In fact, at the end of the reaction there always remains a small amount of esters formed from fatty acids and this alcohol. One can also use glycerol, but since it is normally not eliminated during the course of reaction, the latter competes with the sucrose and one obtains mixtures which are less rich in combined sucrose. However, its presence during the first phase may be of some interest under certain conditions since it facilitates the formation of soaps, which will be further discussed below.

The catalyst employed during the first stage is, like the catalyst employed in the second stage, a transesterification catalyst, but, it is designated in distinctive manner as an "alcoholysis catalyst", since its nature is not critical and it may be either a basic catalyst or an acid catalyst. Examples of basic catalysts which may be employed are potassium bicarbonate or carbonate, sodium or potassium methylate or ethylate, potassium glycerylate, metallic sodium, sodium or potassium hydroxide, quaternary ammonium hydroxides, such as trimethylbenzylammonium hydroxide. Examples of acid catalysts are: sulphuric acid, phosphoric acid, zinc chloride, magnesium chloride, banzenesulfonic acid, p-toluene-sulfonic acid and macroporous sulfonic ion exchange resins.

As preferred catalysts for the first or alcoholysis phase, one may use potassium bicarbonate or carbonate, potassium hydroxide and potassium ethylate, either individually or in mixtures, but simplicity militates in favor of the use of potassium carbonate alone.

The reagents introduced during the course of the second stage of the process are sucrose, a transesterification catalyst and optionally a potassium soap or substances capable of giving rise to it.

The sucrose (sometimes referred to in the literature and herein as saccharose) is generally in particle form and the size of its particles is not critical. The sucrose may be commercial crystallized sugar which can be crushed in order to obtain particle sizes on the order of 250 microns. Uncrushed crystallized sugar can also be used, but in this case the time of reaction must be increased by about one half hour.

The transesterification catalyst is selected as a basic catalyst having a base of potassium. Use may be made of the following compounds, which can be employed alone or in mixture: potassium bicarbonate or carbonate, potassium hydroxide, potassium methylate or ethylate and potassium glycerylate. The preferred catalysts are potassium bicarbonate or carbonate and potassium hydroxide. They may be used in mixture. Even more preferably, potassium carbonate is used, possibly mixed with potassium bicarbonate.

The process of the invention does not require extensive dehydration of the raw materials used (triglyceride, sucrose, catalysts) but they should not be too wet. For instance, they desirably contain less than about 0.2% by weight of water, which exists is their customary commercial state.

Also, a certain amount of soaps or soap precursors may be added to the reaction medium before the introduction of the sucrose. It has been found, in fact, that an amount of soaps of about 7 to 10%, based on total weight of reaction medium, is desirable for good reactivity in the second stage. By "soap" there is understood to be intended a potassium soap, that is to say potassium salts of fatty acids having from about 14 to 20 carbon atoms.

Depending on the alcoholysis catalyst selected, there may or may not be a formation of potassium soaps during the first phase or step of the process. If there is no formation of potassium soaps or else a formation of insufficient quantities of soaps, it is recommended that at the end of the first step a potassium soap or a mixture of potassium hydroxide or potassium bicarbonate or carbonate and fatty acids such as myristic, palmitic, stearic acid, etc. be effected.

When calcium carbonate, optionally mixed with the other catalysts mentioned above, is used in the first phase or stage as alcoholysis catalyst, a small amount of soaps is formed as a result of the moisture contributed by the reagents, namely triglyceride, sucrose and potassium carbonate. If the content of soaps formed is insufficient, it can be remedied either by adding a small amount of water or by adding a potassium soap or its precursors. One can also recycle the soaps or the fatty acids generally in mixture with glycerides and sucrose esters, which are removed at the end of the reaction by purification operations.

Having set forth the various reagents which can be used in the process of the invention, one of the practical embodiments of the invention will now be described in more detail.

As we have already pointed out, the process of the invention is excellently suited for the obtaining of sucroglycerides which can be used in the field of foods. Therefore, we will set forth the preferred conditions of the invention with due consideration of this use, particularly with respect to the selection of the raw materials, but it will be understood that these conditions can easily be adapted by the man skilled in the art in the event of the preparation of sucroglycerides for any other use.

In the first phase or stage of the process, a triglyceride and an alcohol are reacted in the presence of an alcoholysis catalyst. As preferred raw materials, palm oil or tallow is used as triglyceride, ethanol, possibly containing an addition of glycerol, is used as the alcohol, and potassium carbonate is used as alcoholysis catalyst. The amount of alcohol used is expressed with reference to the amount of triglyceride and is such that there is approximately a ratio of three to one between the number of ester functions and the number of alcohol functions. Therefore, there is always a deficit of alcohol.

In order to obtain good reactivity of the triglyceride during the second stage or phase, the optimum content of ethanol is close to one mol of ethanol to 1 mol of triglyceride, namely about 5% by weight of triglyceride.

The percentage of the fatty acid ethyl esters formed at the end of the alcoholysis reaction represents about 20% of the weight of the mixture obtained.

At the end of the second reaction step, the percentage of the said esters is no more than about 2 to 7%. If it is desired to employ a lower percentage without thereby prolonging the duration of the second phase, it is necessary to select an alcoholysis catalyst which contains ethanol and glycerol, namely, for instance, 0.7 mol of ethanol and 0.1 mol of glycerol.

Therefore, an alcohol, preferably ethanol, in an amount representing from about 2 to 30% of the weight of triglyceride, and preferably about 4 to 5%, and optionally glycerol in an amount between 0 to about 5% of the weight of triglyceride, and preferably about 1 to 2%, are introduced in the first step or phase of the process.

It is easier to use the same catalyst during the two steps of the process of the invention, for which reason the use of potassium carbonate is recommended as alcoholysis catalyst.

An amount of potassium carbonate of 0.5% of the weight of triglyceride would be sufficient but, as it is generally desired to obtain from this carbonate the amount of soaps necessary in the second step, between about 1.5% and 4% potassium carbonate and, preferably, about 2% is used.

During the first phase of the process, a small amount of soaps is formed as a result of the hydrolysis of the potassium carbonate. As previously mentioned, a soap content of about 7 to 10% of the weight of triglyceride is desirable in order to have good reactivity in the second phase. A higher content, for instance up to about 20%, leads to a very thick reaction mixture, but quantities of soaps of about 3 to 15% are also suitable.

In order to have a percentage of soaps which is within the preferred range, up to about 0.3% water and preferably about 0.1 to 0.2%, can be introduced. The desired content can also be obtained by directly adding, at the end of the first reaction phase, fatty acids or potassium soaps, or a mixture coming, for instance, from purification operations on the final product.

Finally, one of the characteristics of the process of the invention comprises carrying out the second step or phase in a medium which has undergone partial ethanolysis aud contains between about 3 and 15% potassium soaps, and preferably about 7 to 10%.

The first step of the process of the invention consists in bringing together the triglyceride, the ethanol, mixed possibly with glycerol, the water if necessary, and the potassium carbonate, and heating the resultant mixture at atmospheric pressure up to the boiling point of the alcohol, at about 80° C. The condensed alcohol is returned into the reaction medium and the temperature increases as the alcohol is consumed, finally arriving at a temperature of between about 125° and 135° C., which temperature should not be exceeded.

The alcoholysis reaction can also be carried out without drawback under pressure (for instance up to about 10 atmospheres).

The reaction time depends on the amount of catalysts employed. It is normally between about 1½ hours and 4 hours, but a time of about 2 hours to 2½ hours is ample.

In the reaction mixture prepared in this manner, the second stage or phase of manufacture of the sucroglycerides is started by introduction of the sucrose and the transesterification catalyst. The amount of sucrose most commonly used is about 35% of the weight of triglyceride, which corresponds to a molar ratio of sucrose to triglyceride of about 0.85 to 1. This amount is not critical, since it has been found that one tends always to a combined sucrose concentration close to about 12% of the weight of the mixture obtained at the end of the reaction whatever the excess of sucrose used. It, therefore, appears that there is an equilibrium in the reaction mixture. Thus the excess of sucrose has little effect on the final chemical composition. It may be that a final product which contains very little free and combined sucrose is desired, but in general the sucrose is used in a proportion of about 15 to 45%, referred to the weight of triglyceride employed.

The sucrose is advantageously used after it has been crushed so as to obtain, for instance, particle sizes of 250 microns. It the event that it is used in crystallized form as marketed, it is then necessary to lengthen the reaction time by about 30 minutes.

The transesterification catalyst introduced into the second step of the process is preferably potassium carbonate. It assures the dehydration of the medium while forming soaps and maintaining the medium moderately alkaline. Some must remain at the end of the reaction, which requires a rather large initial amount. It is advantageous to use it in the form of a fine powder having particles of a size similar to those of the sucrose.

It is also of interest to use the potassium carbonate possibly mixed with potassium bicarbonate.

The optimal amount of potassium carbonate is about 5 to 6% of the weight of triglyceride. It can be modified as a function of the amount used during the first phase, the total amount not exceeding about 8 to 9% of the weight of triglyceride since otherwise there is a needless increase in the final content of soaps. A total amount of potassium carbonate of at least about 6% of the weight of triglyceride is necessary if it is desired to reach the final equilibrium in combined sucrose.

The distribution of the quantities of potassium carbonate introduced during the first and second stages is not immaterial and it is advisable to introduce at least half thereof during the second step of the process.

During the second step of the process, the sucrose and additional potassium carbonate are introduced into the reaction mass, which is maintained under agitation. This introduction is effected at a temperature between about 110° and 140° C., and preferably about 120° and 130° C. It is preferable to exclude air from the reaction medium as it causes oxidation reactions resulting in a browning of the finished product, imparting to it a disagreeable odor, and furthermore it involves an additional consumption of catalyst.

The atmosphere above the reaction mixture is maintained inert by means of introducing nitrogen or rare inert gases. It is preferable to effect the sweeping with inert gas, preferably, in depth in the reaction mass but operation in an inert atmosphere is not of an indispensible nature. The blowing of the inert gas is effected at a rate of, for instance, between about 0.5 and 10 liters per hour per liter of reaction mixture or bath, and preferably about 1 liter per hour.

Furthermore, it is preferable to carry out the reaction under reduced pressure during all or part of the reaction time since this assists in the decomposition of the fatty acid ethyl esters formed, thus liberating the alcohol and the fatty acid radicals which then combine more easily with the free sucrose.

One will, therefore, operate at a pressure between about 100 mm. of mercury and atmospheric pressure, and preferably in the vicinity of about 150 mm. Hg pressure. A pressure below 100 mm. is not necessary and disturbs the condensation and recovery of the alcohol liberated. The reduced pressure must be established gradually since rather stable fine foams are formed otherwise.

The introduction of sucrose and potassium carbonate should not be effected suddenly unless the reaction mixture is subjected to vigorous agitation in order to avoid agglomeration of the sucrose. One preferred embodiment of the invention consists in simultaneously introducing the sucrose and the potassium carbonate continuously, or batchwise, for a period extending from about 10 minutes to 2 hours, and preferably about 30 minutes.

Towards the end of the introduction of the sucrose and potassium carbonate, the reaction temperature is increased. The reaction time will depend on this temperature and also on the final color. It will be between about 120° and 145° C., the preferred range being from about 130° to 135° C.

At a temperature of about 130° to 135° C., the reaction starts rapidly and in two hours 7 to 8% combined sucrose is obtained. The velocity then slows down upon approaching the equilibrium which is close to 12% at the same time as the color increases. After 6 hours, the reaction does not proceed further. The total time of the second reaction step is about 2 to 6 hours and preferably about 4 to 5 hours.

The preferred conditions for the carrying out of the process of the invention comprise:

(1)—in heating, at reflux temperature under atmospheric pressure for about 2 to 2½ hours, the triglyceride, preferably natural triglyceride, with ethanol in the presence of potassium carbonate, with optionally the addition of a small amount of water which leads to the formation of potassium soaps;

(2)—in introducing the sucrose and further potassium carbonate continuously for a period of about 30 minutes into the reaction medium with agitation at a temperature of about 120° to 130° C., the mixture being maintained under an inert gas atmosphere, and then increasing the temperature to between about 130° and 135° C., while establishing a reduced pressure of about 150 mm. Hg and continuing the heating until obtaining a reaction time of from about 4 to 5 hours.

The preparation of the sucroglycerides may be carried out in a conventional apparatus, which therefore has nothing special about it. The reactor employed should be provided with a heating device, a cooling system and the customary means for the monitoring of the reaction (e.g., thermometer, pressure gauge). It is provided with means for the introduction of the reagents, an inert gas inlet preferably extending into the reaction mass, apparatus if necessary for assuring reduced pressure and some mechanical means of agitation (e.g., propeller, blade, turbine, etc.). The agitation need not be very rapid—it is a question of maintaining the excess sucrose and catalyst in suspension and of permitting heat exchanges. However, more powerful or diversified means of agitation may be employed, such as micronizer or circulation of inert gas. On top of the reactor there is arranged a condensor providing possibly for reflux of the condensate into the reactor.

By the process of the invention, there are obtained sucroglycerides containing combined sucrose in an amount which tends in all cases towards 12% whatever the excess of sucrose used. Without the method of the invention being limited to this assumption, it would appear probable that the essential characteristic of the process of the invention is step (I) which permits step (II) to take place rapidly. In fact, during step (I), a mixture of monoglycerides and diglycerides, potassium soaps and ethyl esters of fatty acids is formed. This mixture has the property of permitting the sucrose to react rapidly in step (II). It does not appear that it is the true solubility of the sucrose in the medium of step (I) which increases its reactivity, but the hypothesis of formations of molecular associations has been advanced. According thereto, there is formed a ternary molecular association of sucrose, diglycerides and potassium soaps capable of developing internally into a molecular association of sucrose monoesters, monoglycerides and potassium soaps; together also with other molecular associations of the same type—sucrose—monoglycerides-potassium soaps; glyceroldiglycerides-potassium soaps, etc.

The importance of the first step of preparation of the medium and of the concentration ratios which lead to optimal conditions is then evident.

The reaction stops when it approaches the reaction equilibrium, which probably corresponds to the equilibrium imposed within the molecular associations.

The reaction of the process of the invention makes it possible to obtain a mixture referred to as "sucroglycerides", which contains sucrose esters, free sucrose, potassium soaps, glycerides, free glycerol, fatty acid alkyl esters and potassium carbonate and bicarbonate.

Generally the mixture obtained has the following composition:

sucrose esters between about 15 to 35%, including about 7 to 20% sucrose monoesters.

free sucrose: about 10 to 35%.

potassium soaps: about 14 to 20%.

glycerides: about 30 to 50%, including about 5 to 15% of triglycerides.

free glycerol: about 0.5 to 1%.

fatty acid alkyl esters: 1 to 7%.

potassium carbonate: about 0.5 to 2%.

potassium bicarbonate: about 2 to 4%.

It is either cast and used as is or neutralized, more or less strongly depending on the pH desired, with, for instance, acetic, phosphoric, citric or lactic acids. It may be purified by the customary methods suitable for eliminating the soaps and recovering the excess saccharose. The final product may also be subjected to discoloration or to a concentration of saccharose esters.

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, and throughout the specification, the quantities of material are expressed in terms of parts by weight, unless otherwise specified.

Reference will now be had to Examples 1 to 17, below, in order to provide a fuller understanding of the present invention and the carrying out thereof in practice.

By way of comparison, two tests were carried out: one (A) directed at proving the existence of a physico—chemical equilibrium in the medium, and the other (B) concerning the preparation of sucroglycerides by a transesterification method but without a prior alcoholysis step of the present invention.

In the examples, the analytical methods used to follow the course of the reaction in a very complicated medium were the following:

(a)—determination of the free and combined sucrose: the sample was dissolved in a hexane-ethanol mixture and the free sucrose was extracted with salt water. The organic layer was concentrated by evaporation and the residue was subjected to a saponification which liberates the sucrose. The amount of sucrose was determined by a colorimetric method with anthrone (M. N. Halhoul et al., "Anal. Biochem." 50, 337–343 (1972)).

(b)—determination of the fatty acid alkyl esters: this was effected by gas-phase chromatography;

(c)—determination of the potassium soaps: this was effected by the conventional acidimetric method after elimination of the carbonates by washing with salt water.

The percentages expressed in the following examples are percentages by weight.

EXAMPLE 1

In this example the sucroglycerides are obtained from palm oil and sucrose, used in accordance with the process of the invention.

The palm oil, subjected to saponification, gave the following analytical results:

| | |
|---|---|
| Acidity | 1.5 to 2 × $10^{-3}$ M/kg |
| Water | $\leq 0.01\%$ |
| Iodine number | 52.8–53.3 mg. of $I_2$/100 g |
| Total glycerol | 10 to 11% |
| Free glycerol | 0.07% |
| Distribution of the acids in the palm oil: | |
| Light | 0.65% |
| C 14 myristic acid | 1.35% |
| Intermediate | 0.06% |
| C 16 palmitic acid | 45% |
| Intermediate | 0.25% |
| C 18 stearic acid | 5.25% |
| C 18' oleic acid | 36.75% |
| C 18" linoleic acid | 9.6% |
| Heavy | 1.1% |

Into a three-liter three-neck flask provided with an agitator with two flat blades which were located towards the bottom and turn at 700 rpm, heated by an oil bath, there were introduced:
1 kg of palm oil
25 kg of potassium carbonate
60 g of anhydrous ethanol
2 g of water A reflux condenser was placed on the flask and the flask was heated so as to maintain the contents at a slight boil. The temperature rose from 85° to 125° C., which temperature was maintained. The total time was two hours.

The flask was provided with a goose neck with condensor and receiver to collect the condensate.

A nitrogen atmosphere was produced by bubbling a stream of nitrogen at a rate of 1 liter per hour through the reaction medium via a dip tube.

A sample taken from the reactor showed a soap content of 9% (calculated as potassium palmitate) and 21% ethyl esters (ethyl palmitate and oleate).

The bath was held at 125° C., and 300 g of sucrose, crushed to 250 microns, and 50 g of potassium carbonate were added in small fractions over the course of 30 minutes.

The pressure was then progressively increased during the course of one hour to 150 mm. Hg, avoiding the rising of the foam, while the temperature was increased to 130° to 135° C.

A sample taken two hours after the start of the addition of the saccharose showed 8% combined sucrose and, after 5 hours, 11.5%. The soap content was then 18% and the content of ethyl esters 4%.

The reaction mass was cooled at 110° C. and partially neutralized with 60 g. of finely crushed citric acid, and then set aside for 30 minutes before being cast.

The solidified product was of a light brown, waxy appearance and has emulsifying properties similar to a purified commercial sucroglyceride prepared by means of dimethylformamide (CELYNOL MSPO 11), the composition of which was:

| | |
|---|---|
| combined sucrose | 19.2% |
| free sucrose | $\leq 1.5\%$ |
| soaps | $\leq 5\%$ (sodium salt) |
| glycerides | 42.4% including 1.8% triglycerides |
| sucrose esters | 49.7% |

EXAMPLE 2

This example shows the influence of the amount of ethanol used during the first reaction phase or step.

The same procedure was used as in Example 1, except that 240 g of ethanol were introduced, instead of 60 g.

At the end of the ethanolysis, the mixture contained 46% ethyl esters.

In the second step or phase, after two hours of reaction there was 3% combined sucrose and, after 5 hours, 7%, and 20% ethyl esters remained.

The reaction mass was more colored than in Example 1.

EXAMPLE 3

This example shows how the soap content is decreased when no water is used during the ethanolysis.

The conditions were the same as in Example 1, except that no water was introduced.

At the end of the ethanolysis, the soap content was 4%.

After two hours of reaction, there was 5.5% combined sucrose. After 5 hours, the soap content was 14% and the content of combined sucrose was 9.5%.

The product was cooled to 100 C. and neutralized with 20 g of acetic acid.

It had an emulsifying power which was slightly less than that of the aforementioned commercial product.

EXAMPLE 4

The variant which consists in adding soap percursors at the end of the ethanolysis is illustrated below.

The manner of operation described in Example 3 was repeated.

At the end of the ethanolysis, 10 g of potassium carbonate and 40 g of stearic acid were added and the mixture was set aside at 125° C. for 30 minutes.

The reaction with the sucrose was then carried out in the same manner as in Example 1, but using only 40 g of potassium carbonate.

The final product was analogous in its analyses and properties to that of Example 1.

EXAMPLE 5

This example illustrates the use of a mixture of ethanol and glycerol in order to effect the alcoholysis of the palm oil.

The same procedure was employed as in Example 1, but only 40 g of ethanol were introduced and, in addition, 13 g of glycerol.

At the end of the ethanolysis, there were 16% ethyl esters.

After 5 hours of reaction with the sucrose, 2% ethyl esters remained and there was 11% combined saccharose and 17% soaps.

EXAMPLE 6

In this example all of the ethanol was replaced by glycerol.

The 60 g of ethanol of Example 1 were replaced by 40 g of glycerol.

At the end of the alcoholysis there were, of course, no ethyl esters but a mixture of mono-, di- and tri-glycerides, containing 8.5% soaps.

After reaction for 1 hour with the sucrose, there was already 7% combined sucrose, but after 5 hours there was only 9%.

EXAMPLE 7

This example shows the influence of the manner of introducing the potassium carbonate.

The same procedure was used as in Example 1, but the total amount of potassium carbonate, that is to say 75 g, was introduced at the very start of the first step or phase. At the end thereof there were 13% soaps and the medium was very thick.

After two hours of reaction with the sucrose, there was 7% combined sucrose, but after 5 hours there was only 7.5%.

EXAMPLE 8

The influence of the rate of introduction of the reagents, sucrose and potassium carbonate, during the second phase is shown by this example.

The operating conditions of Example 1 were repeated, with the exception of the addition, at the start of the second step, of the sucrose and carbonate, which was effected in 2 to 3 minutes.

Stickly masses were formed along the agitator and on the bottom of the flask and caramelized rapidly. The reaction in the liquid phase was practically zero.

EXAMPLE 9

In this example the amount of potassium carbonate during the second phase was modified.

35 g of potassium carbonate were introduced instead of 50 g during the reaction with the sucrose.

After two hours of reaction there was 6.5% combined sucrose and after 5 hours only 8%. 14% soaps were found.

EXAMPLE 10

This example illustrates the use of another catalyst composed of potassium carbonate and potassium bicarbonate.

In the first step, the 25 g of potassium carbonate were replaced by 7 g of potassium carbonate and 45 g of potassium bicarbonate, and no water was added. At the end of the ethanolysis, there were 20% ethyl esters and 8% soaps.

90 g of potassium bicarbonate were introduced with the sucrose instead of 50 g of potassium carbonate. After two hours of reaction, there was only 4.5% combined sucrose but there was 11.5% after 5 hours. There was 22% soaps.

EXAMPLE 11

A smaller amount of sucrose was used than in Example 1, operations under the same conditions but the 300 g of sucrose were replaced by 150 g.

After two hours of reaction, there was 6% combined sucrose and, after 5 hours, 9.5%.

EXAMPLE 12

This example illustrates the use of an excess of sucrose.

The procedure of Example 1 was repeated, but 450 g of sucrose were used instead of 300 g.

11.5% of combined sucrose was obtained after 5 hours of reaction.

EXAMPLE 13

The preparation of the sucroglycerides was carried out in accordance with the conditions described in Example 1, but the temperature of reaction with the sucrose was changed, it now being maintained higher, at 140° to 145° C.

After two hours of reaction, there was 9.5% combined sucrose and after 5 hours there was 10.5% thereof and 18% soaps. The product was very colored.

EXAMPLE 14

As compared with the preceding example and Example 1, the reaction temperature with the sucrose was lower, being now maintained at 120° to 125° C.

After two hours of reaction, there was 6% combined sucrose and after 5 hours there was only 9% thereof and 17% soaps. 7% ethyl esters remain and the product was only slightly less colored than in Example 1.

EXAMPLE 15

The same procedure is used as in Example 1, but reaction step (II) was carried out at atmospheric pressure.

After two hours of reaction, there was 11.5% combined sucrose, but 14% ethyl esters.

EXAMPLE 16

The experiment was carried out in a manner identical to that described in Example 1, but without working under an inert gas atmosphere.

After 5 hours of reaction, the percentage of combined sucrose was only 9.5% and the product obtained was slightly more colored.

EXAMPLE 17

This example illustrates the use of another triglyceride, namely tallow.

The same procedure was used as in Example 1, except that the palm oil was replaced by a purified tallow.

At the end of the ethanolysis, there was 8.5% soaps (calculated as potassium stearate) and 22% ethyl esters (ethyl stearate and oleate).

After 5 hours of reaction with the sucrose, there was 10.5% combined sucrose, 3% ethyl esters and 19% soaps.

The reaction mixture was cooled to 75° C. and diluted with 3 kg. of ethyl acetate. Filtration was effected at 60° C., there being recovered 100 g of recyclable free sucrose. The filtrate was partially neutralized with 20 g of phosphoric acid.

After evaporation of the ethyl acetate, the product obtained had emulsifying properties similar to those of a commercial product prepared from tallow in a dimethylformamide medium.

Two comparative tests referred to above were as follows:

TEST A

This test shows the existence of a reaction equilibrium, by subjecting a sucroglyceride obtained by the solvent method to the operating conditions of the process of the invention.

1 kg of sucroglycerides obtained by a dimethylformamide process, and the characteristics of which have already been given, was introduced into the reactor described above. 70 g of potassium carbonate were added and heating was effected to 130° C. The initial product contained 19.2% combined sucrose. The combined sucrose content decreased to 12.5% at the end of the 30 minutes, 12% after 1 hour and was still 12% after 5 hours. The soaps were determined as 21%.

TEST B

In this test there is shown the important role played by the first alcoholysis phase of the process of the invention.

By way of comparison, a preparation was effected without prior ethanolysis.

1 kg of palm oil, 300 g of sucrose and 100 g of potassium carbonate were reacted. The reaction medium was continuously agitated and brought to a temperature of 130° C. It was maintained under a nitrogen atmosphere and under reduced pressure of 150 mm Hg. After 4 hours there was less than 0.5% combined sucrose and after 6 hours there was 5% thereof. It was noted that the initiation phase was very slow. After 9 hours of reaction, 9.5% combined sucrose and 23% soaps were obtained. The product was very colored, showing thermal decomposition of the sucrose.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What is claimed is:

1. A process of preparing sucroglycerides, which comprises the steps of reacting a triglyceride and an alcohol selected from the group consisting of ethanol and mixtures of ethanol and glycerol, the amount of said ethanol being between about 2% and 30% of the weight of said triglyceride, in the presence of an alcoholysis catalyst at a temperature of between about 80° and 180° C and introducing to that reaction mixture sucrose and a basic transesterification catalyst while maintaining the mixture at a temperature of between about 120° and 145° C.

2. A process according to claim 1, wherein the triglyceride and alcohol are reacted at pressure above atmospheric.

3. A process according to claim 1, wherein the reaction with the sucrose is conducted at reduced pressure.

4. A process according to claim 1, wherein at least one fatty acid triglyceride having about 14 to 20 carbon atoms is employed.

5. A process according to claim 4, wherein the triglyceride employed is a member selected from the class consisting of palm oil and tallow.

6. A process according to claim 1, wherein the transesterification catalyst is a basic catalyst with a base of potassium.

7. A process according to claim 1, wherein the alcoholysis catalyst comprises a member selected from the class of the following compounds, alone or in mixture: potassium bicarbonate, potassium carbonate, potassium hydroxide, and potassium ethylate and the transesterification catalyst is a member selected from the class of the following compounds, used alone or in mixture: potassium bicarbonate, potassium carbonate and potassium hydroxide.

8. A process according to claim 7, wherein the alcoholysis catalyst is potassium carbonate and the transesterification catalyst is potassium carbonate.

9. A process according to claim 1 wherein the amount of glycerol is between about 0% and 5% of the weight of triglyceride.

10. A process according to claim 9, wherein the amounts of ethanol and glycerol represent about 4 to 5% and about 1 to 2%, respectively, of the weight of triglyceride.

11. A process according to claim 1, wherein potassium carbonate is employed in the alcoholysis step and represents about 1.5 to 4% of the weight of triglyceride.

12. A process according to claim 11, wherein the amount of potassium carbonate used in the alcoholysis step is about 2%.

13. A process according to claim 11, wherein the amount of soaps present in the second step is between about 3 and 15% of the weight of triglyceride.

14. A method according to claim 13, wherein the amount of soaps is about 7 to 10% of the weight of triglyceride.

15. A process according to claim 13, wherein the soap content is obtained by addition of water up to about 0.3% of the weight of triglyceride.

16. A process according to claim 13, wherein the soap content is obtained by addition of water in the amount of about 0.1 to 0.2% of the weight of triglyceride.

17. A process according to claim 15, wherein the triglyceride, alcohol, and potassium carbonate are heated to reflux temperature under atmospheric pressure for about 1½ to 4 hours.

18. A process according to claim 1, wherein the duration of the alcoholysis reaction is between about 2 hours and 2½ hours.

19. A process according to claim 13, wherein at least a portion of the soap content is obtained by the addition of a potassium soap or substances capable of giving rise thereto to the mixture at the end of the alcoholysis reaction step before the introduction of the sucrose.

20. A process according to claim 1, wherein the amount of sucrose represents from about 15 to 45% of the weight of triglyceride.

21. A process according to claim 17, wherein the amount of potassium carbonate added to the second step represents from about 5 to 6% of the weight of triglyceride.

22. A process according to claim 21, wherein the total amount of potassium carbonate introduced during the two steps represents from about 6 to 9% of the weight of triglyceride.

23. A process according to claim 22, wherein the sucrose and further potassium carbonate are introduced into the reaction mixture continuously for a period of time ranging from about 10 minutes to 2 hours with agitation at a temperature of about 110° to 140° C., the reaction mixture being maintained under an inert-gas atmosphere, the temperature is then increased to between about 120° and 145° C., while establishing a reduced pressure of between about 100 mm Hg and atmospheric pressure and the heating is continued for a time ranging from 4 to 5 hours.

24. A process according to claim 23, wherein the sucrose and further potassium carbonate are introduced continuously for a period of about 30 minutes into the reaction mixture with agitation, and at a temperature of about 120° to 130° C., the reaction mixture being maintained under an inert-gas atmosphere, that the temperature is increased to between about 130° and 135° C., while establishing a reduced pressure of about 150 mm Hg, and that the heating is continued until obtaining a reaction time ranging from 4 to 5 hours.

* * * * *

UNITED STATES PATENT AND TRADEMARK OFFICE
CERTIFICATE OF CORRECTION

PATENT NO. : 4,377,685
DATED : March 22, 1983
INVENTOR(S) : Bouniot et al.

It is certified that error appears in the above—identified patent and that said Letters Patent is hereby corrected as shown below:

At column 1, line 47, "in" should be --is--.

At column 2, line 36, "present" should be --process--.

At column 2, line 38, delete "a" immediately after "is".

Signed and Sealed this

Fifth Day of February 1985

[SEAL]

Attest:

DONALD J. QUIGG

Attesting Officer        Acting Commissioner of Patents and Trademarks